(12) United States Patent
Klein et al.

(10) Patent No.: US 9,259,398 B1
(45) Date of Patent: Feb. 16, 2016

(54) BIOACTIVE AGENT-LOADED TARGETING MICELLES

(75) Inventors: Kyle Klein, San Jose, CA (US); Katsuyuki Murase, Cupertino, CA (US); Jinping Wan, Sunnyvale, CA (US); Dariush Davalian, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 1149 days.

(21) Appl. No.: 12/324,618

(22) Filed: Nov. 26, 2008

Related U.S. Application Data

(60) Provisional application No. 60/990,716, filed on Nov. 28, 2007, provisional application No. 60/990,234, filed on Nov. 26, 2007.

(51) Int. Cl.

| | |
|---|---|
| *A61K 9/50* | (2006.01) |
| *A61K 51/00* | (2006.01) |
| *A01N 25/28* | (2006.01) |
| *A61K 31/00* | (2006.01) |
| *A61K 38/00* | (2006.01) |
| *A61K 39/44* | (2006.01) |

(52) U.S. Cl.
CPC ............. *A61K 31/00* (2013.01); *A61K 38/00* (2013.01); *A61K 39/44* (2013.01)

(58) Field of Classification Search
CPC . A61K 31/00; A61K 38/44; A61K 39/39558; A61K 9/14; A61K 9/127; A61K 9/0019; A61K 41/00; A61K 45/06; A61K 49/0082; A61K 49/0093; A61K 49/085; A61K 47/48415; A61K 47/48546; A61K 47/48569; A61K 47/48859; A61K 51/00; A61K 51/0482; A61K 51/0497; A61K 2039/00; A61K 2039/505; A61K 2039/54; A61K 2039/60; A61K 2039/62; A61K 2039/64; A61K 2236/00; A61K 2300/00

See application file for complete search history.

(56) References Cited

U.S. PATENT DOCUMENTS

| | | | |
|---|---|---|---|
| 5,443,495 A | 8/1995 | Buscemi et al. | |
| 6,524,552 B2 * | 2/2003 | Klaveness et al. | 424/1.85 |
| 6,663,881 B2 | 12/2003 | Kunz et al. | |
| 2001/0021703 A1 * | 9/2001 | Kosak | 514/58 |
| 2002/0086896 A1 * | 7/2002 | Kunz et al. | 514/449 |
| 2002/0128195 A1 * | 9/2002 | Zalipsky | 514/12 |
| 2004/0162275 A1 * | 8/2004 | Yui et al. | 514/183 |
| 2004/0248856 A1 * | 12/2004 | Lanza et al. | 514/124 |
| 2006/0069069 A1 * | 3/2006 | Kajander et al. | 514/89 |
| 2007/0253901 A1 * | 11/2007 | Deng et al. | 424/1.69 |

FOREIGN PATENT DOCUMENTS

WO   WO 2006/135415 A2   12/2006

OTHER PUBLICATIONS

Vlerken et al., (Expert Opin Drug Deliv. Mar. 2006. vol. 3(2):205-216).*
Yoo et al., (J. of Controlled Release. 2002. vol. 82:17-27).*
Orlova et al., (Cancer Research. Apr. 15, 2006. vol. 66(8):4339-4348).*
Veronese et al., (Drug Discovery Today. 2005. vol. 10(21):1451-1458).*
Hamilton et al (J of American College of Cardiology (2004. vol. 43(3):453-460.*
Uwatoku et al., (Circulation Res. 2003. vol. 92:e62-e69).*
Berkowski et al., "Ultrasound-Induced Site-Specific Cleavage of Azo-Functionalized Poly(ethylene glycol)", Macromolecules 38, pp. 8975-8978 (2005).
Hermanson, Bioconjugate Techniques $2^{nd}$ Ed. (book) table of contest, 18 pgs. (2008).
Kim et al., "Polymeric worm micelles as nano-carriers for drug delivery", Nanotechnology 16, pp. S484-S491 (2005).
Nasongkla et al., "Multifunctional Polymeric Micelles as Cancer-Targeted, MRI—Ultrasensitive Drug Delivery Systems", Nano Letters vol. 6, No. 11, pp. 2427-2430 (2006).
Torchilin, "Micellar Nanocarriers: Pharmaceutical Perspectives", Pharm. Res. vol. 24, No. 1, 16 pgs. (2007).
Zhang et al., "Molecular Profiling of Heart Endothelial Cells", Circulation, pp. 1601-1611 (2009).
Zhang et al., "Pharmaco attributes of dioleoylphosphatidylethanolamine/cholesterylhemisuccinate liposomes containing different types of cleavable lipopolymers", Pharm. Res. vol. 49, pp. 185-198 (2004).
Kirpotin et al., "Liposomes with detachable polymer coating: destabilization and fusion of dioleoylphosphatidylethanolamine vesicles triggered by cleavage of surface-grafted poly(ethylene glycol)", FEBS Letters 388 pp. 115-118 (1996).
Madea et al., "A reduction-triggered delivery by a liposomal carrier possessing membrane-permeable ligands and a detachable coating", Coloids and Surfaces B: Biointerfaces 49, pp. 15-21 (2006).

* cited by examiner

*Primary Examiner* — Ja'na Hines
(74) *Attorney, Agent, or Firm* — Squire Patton Boggs (US) LLP

(57) ABSTRACT

A composition of bioactive agent-loaded micelles with tissue-targeting properties and methods of using the same are disclosed.

14 Claims, No Drawings

BIOACTIVE AGENT-LOADED TARGETING MICELLES

RELATED APPLICATIONS

This application claims the benefit of U.S. Provisional Patent Applications Ser. Nos. 60/990,716 filed Nov. 28, 2007, and 60/990,234 filed Nov. 26, 2007, both of which are incorporated by reference as if fully set forth herein.

FIELD OF THE INVENTION

The present invention relates to a bioactive agent-containing micelle with a targeting moiety appended to its surface, and methods of using same for treating vascular disease.

BACKGROUND OF THE INVENTION

In healthy vasculature, vessel walls are composed of an endothelial cell lining, a medial layer of vascular smooth muscle cells and an over layer of connective tissue. The endothelial cell lining is ideally situated at the interface between the blood and the vessel wall to transduce signals, with endothelial cells controlling the homeostatic balance of the vessel through the production of factors regulating processes such as vessel tone, coagulation state, cell growth, cell death, and leukocyte trafficking. Vascular smooth muscle cells maintain the contractile tone of the blood vessel in response to vasoactive agents, and release cytokines and other growth factors. In conjunction with fibroblasts, the smooth muscle cells produce extracellular matrix proteins and proteases that determine vessel structure. Occlusive vascular disease, the most common form of which is atherosclerosis, is characterized by an abnormal accumulation of lipid, inflammatory cells, vascular smooth muscle cells and extracellular matrix proteins within the intimal space between the endothelial lining and the medial layer (plaque formation).

Therapies for atherosclerosis can arrest or reverse the process of plaque formation or stimulate the formation of new blood vessels. Systemic administration of therapies, however, commonly results in undesirable side effects due, for example, to generalized toxic effects throughout the entire body. Indeed, side effects can limit the utility of existing pro-angiogenic therapies for treatment of vascular disease.

As the cells which make up the internal lining of blood vessels, endothelial cells are the first cell type encountered by a circulating drug or other substance. Endothelial cells therefore provide an excellent target for selectively directing a therapeutic substance to the vasculature, including cardiac tissues. Indeed, such selective targeting of a therapeutic substance would help reduce or eliminate the risk of unwanted side effects such as systemic toxicity or malignant transformation. Selective targeting would also cause a high local concentration of the substance, thereby reducing the dosage required for effective treatment. There is therefore, a need for treatments using such selective targeting.

The present invention provides a micelle composition able to selectively target the vasculature, including cardiac tissues, and methods of using such a composition for treating a vascular disease.

SUMMARY OF THE INVENTION

Thus, an aspect of the present invention is a composition comprising a micelle; a bioactive agent encapsulated within, adhered to a surface of or integrated into the structure of the micelle; a targeting ligand covalently bound to or integrated into the surface of the micelle; or a chelating agent covalently bound to or integrated into the surface of the micelle; and a poly(ethylene glycol) group operatively coupled to the surface of the micelle through a cleavable linker.

In an aspect of the present invention, the targeting ligand is selected from the group consisting of a polypeptide, a protein, an oligonucleotide, a lipid, a carbohydrate, a folate residue, a short chain alkyl group and combinations thereof.

In an aspect of this present invention, the polypeptide is selected from the group consisting of a cysteine-arginine-proline-proline-arginine (CRPPR) polypeptide or a peptidomimetic or homolog thereof, an ApoA1 mimetic peptide, an arginine-glycine-aspartic acid (RGD) sequence and an antibody fragment.

In an aspect of this invention, the protein comprises an antibody or antibody fragment selected from the group consisting of an anti-intercellular adhesion molecule, an anti-vascular cellular adhesion molecule, an anti-integrin, an anti-platelet endothelial cell adhesion molecule, an anti-thrombomodulin, an anti-E-selectin, an anti-P-selectin, and anti-L-selectin, an anti-fibronectin, an anti-sialyl-Lewis glycan, an anti-endothelial clycocalyx protein, an anti-cadherin, an anti-vitronectin and combinations thereof.

In an aspect of this invention, the protein comprises an affibody.

In an aspect of this invention, the oligonucleotide comprises an aptamer.

In an aspect of this invention, the aptamer is selected from the group consisting of an anti-junction adhesion molecule and an anti-leukocyte adhesion molecule.

In an aspect of this invention, the lipid is selected from the group consisting of a fatty acid and derivates thereof.

In an aspect of this invention, the fatty acid is selected from the group consisting of oleic acid and stearic acid.

In an aspect of this invention, the fatty acid derivative is ceramide.

In an aspect of this invention, the chelating agent is selected from the group consisting of ethylenediamine tetraacetic acid, diethylenetriamine pentaacetic acid, N-(2-hydroxyethyl)ethylenedinitrilotriacetic acid, nitrilotriacetic acid, citrate, tetracycline, ethylene diamine disuccinic acid, ethylene diaminebis, O-hydroxyphenyl acetic acid and ethylene diamine-N,N' diacetic acid, derivatives thereof and combinations thereof.

In an aspect of this invention, the cleavable linker is selected from the group consisting of a photoreactive moiety, an ester, an azo linkage, a hydrazone, an orthoester, a boron complex, an imino carbonate, a Schiff base, a hemi-acetal, an acetal, a ketal, a hemi-ketal, an enzymatically cleavable peptide, an analyte-receptor complex, a group susceptible to oxidative cleavage, or a group susceptible to reductive cleavage.

In an aspect of this invention, the cleavable linker further comprises a hydrophobic lipid anchor.

In an aspect of this invention, the hydrophobic lipid anchor comprises a biocompatible, degradable polymer.

In an aspect of this invention, the biodegradable polymer is selected from the group consisting of poly(lactic acid), poly(glycolic acid), poly(L-lactic acid), poly(DL-lactic acid), poly(lactic-co-glycolic acid), poly(butyl acrylate), polycaprolactone and parylene.

In an aspect of this invention, the hydrophobic lipid anchor comprises a lysolipid or a di-acyl phospholipid.

In an aspect of this invention, the analyte-receptor complex comprises streptavidin-biotin.

In an aspect of this invention, the cleavable linker comprises a cyclodextrin complex.

In an aspect of this invention, the bioactive agent is selected from the group consisting of an anti-stenosis agent, an anti-proliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor and combinations thereof.

An aspect of this invention is an implantable medical device comprising: a device body; and a composition according to claim 1 disposed over the device body.

In an aspect of this invention regarding the above implantable medical device the device body comprises a stent.

An aspect of this invention is a method for treating or preventing a disease comprising implanting a medical device of this invention in a patient in need thereof.

An aspect of this invention is a method for treating or preventing a disease comprising providing a composition of this invention and administering a therapeutically effective amount of the composition to a patient in need thereof.

In an aspect of this invention, in the above method, administering the composition comprises intra-arterial delivery.

In an aspect of this invention, in the above method, intra-arterial delivery comprises percutaneous transluminal coronary arterial delivery.

In an aspect of this invention, in the above method, intra-arterial delivery comprises using a catheter.

In an aspect of this invention, in the above method, the disease comprises a vascular disease selected from the group consisting of atherosclerosis, stenosis, restenosis and vulnerable plaque.

DETAILED DESCRIPTION OF THE INVENTION

It is understood that use of the singular throughout this application including the claims includes the plural and vice versa unless expressly stated otherwise. That is, "a" and "the" are to be construed as referring to one or more of whatever the word modifies. Non-limiting examples include: "a therapeutic agent," which is understood to include one such agent, two such agents or, under the right circumstances, as determined by those skilled in the treatment of diseased tissues, even more such agents unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended. And "a poly(ethylene glycol) group" refers to one or more, potentially many more, such groups.

In many instances, localized intravascular administration of bioactive agents would comprise a significant improvement in the art. There are, however, special considerations that must be taken into account in the development of a localized, intravascular bioactive agent-delivery system. For example, the system should not promote clotting or thrombogenesis. Moreover, the system should take into account that constant blood flow through the vasculature may result in rapid dilution of the bioactive agent. The present invention mitigates these issues by providing a composition containing bioactive agent-loaded micelles that preferentially localize to a diseased tissue such as, without limitation, an atherosclerotic lesion or an infarcted myocardial tissue.

Specifically, the present invention relates to a composition that includes a plurality of micelles, one or more bioactive agents encapsulated within, adhered to a surface of or integrated into the structure of the micelles and one or more targeting moieties agents covalently bound to or integrated into the surface of the micelles.

As used herein, "micelle" refers to a supramolecular aggregate of amphipathic molecules which form spherical colloidal nanoparticles spontaneously when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5 nm to about 50 nm, micelles have been shown to exhibit spontaneous accumulation in pathological areas with leaky vasculature and impaired lymphatic drainage, a phenomenon known as the Enhanced Permeability and Retention or EPR effect.

The problem with micelles formed from relatively low molecular weight surfactants is that their CMC is usually quite high so that the formed micelles dissociate rather rapidly upon dilution, i.e., the molecules head for open places at the surface of the water with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMCs as low as $10^{-6}$ M (molar). Thus, they tend to be very stable while at the same time showing the same beneficial characteristics as surfactant micelles. Any micelle-forming polymer presently known in the art or as such may become known in the future may be used in the method of this invention. Since micelles are nano-scale particles, they may be administered using the porous balloon discussed above as well as in polymeric matrices. Examples of micelle-forming polymers are, without limitation, methoxy poly(ethylene glycol)-b-poly(ε-caprolactone), conjugates of poly(ethylene glycol) with phosphatidylethanolamine, poly(ethylene glycol)-b-polyesters, poly(ethylene glycol)-b-poly(L-aminoacids), poly(N- vinylpyrrolidone)-bl-poly(orthoesters), poly(N-vinylpyrrolidone)-b-polyanhydrides and poly(N-vinylpyrrolidone)-b-poly(alkyl acrylates).

In addition to the classical spherical micelles described above, therapeutic agents may be delivered using the methods of this invention in compositions comprising synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly(lactic acid), poly($\epsilon$-caprolactone), poly(ethylethylene) and polybutadiene. A representative description of worm micelle formation, characterization and drug loading can be found in Kim, Y., et al., *Nanotechnology*, 2005, 16:S484-S491. The techniques described there as well an any other that is currently known or may become known in the future may be used in the regional delivery method of this invention.

Any of the above types of micelles are encompassed by the present invention. Micelles may be composed of a range of materials including, but not limited to, biostable polymers, biodegradable polymers, lipids, or a combination thereof. Biostable refers to polymers that are not degraded in vivo. Biodegradable refers to polymers that can gradually break down under the influence of physiological conditions and then can be either safely absorbed and/or eliminated by the body. Of course, any polymer, be it biostable or biodegradable, must also be biocompatible. "Biocompatible" refers to a property of a material characterized by it, or its physiological degradation products, being not, or at least minimally, toxic to living tissue; being not, or at least minimally and reparably, otherwise injurious living tissue; and/or being not, or at least minimally and controllably, causative of an immunological reaction in living tissue. With regard to salts, both the cation and anion must be biocompatible.

Micelles of the invention can also be made of di-, tri- or multi-block copolymers containing hydrophilic and hydrophobic blocks. Examples of hydrophilic blocks include, without limitation, amine-functional polymers, polystyrene sulfonate, polyethers such as, without limitation, poly(ethylene glycol) (PEG) and poly(ethylene oxide) (PEO), vinyl acids, vinyl alcohols and acrylic esters wherein the ester group is substituted with water-soluble groups, predominantly hydroxyl groups. Examples of hydrophobic blocks include, without limitation, PLLA, PLGA, PGA, PCL, poly(L-amino acids) (PAA), poly(vinylidene chloride), polyamides, polyimides, poly(fluorocarbons), polystyrenes, polyolefins, poly(vinyl ethers), poly(vinyl ketones) and phospholipids. The hydrophobic portion can be biodegradable or biostable. Methods of making micelles from di-, tri- or multi-block copolymers are well-known to those skilled in the art.

Micelles of the invention include one or more bioactive agents encapsulated within, adhered to a surface of or integrated into the structure of the micelle.

As used herein, "encapsulated within" means the agent is contained within the space defined by the hydrophobic center of the micelle.

As used herein, "adhered to the surface of" means the agent is covalently or non-covalently coupled to the outer surface of the micelle.

As used herein, "integrated into the structure of" means the agent is part of the chemical structure of the material forming the micelle.

Hydrophobic bioactive agents suspended in an aqueous medium can be entrapped and solubilized in the hydrophobic center of micelles, which can result in an increase in agent bioavailability as well as improve agent stability, thereby improving the pharmacokinetics and possibly decreasing agent toxicity.

As used herein, "bioactive agent" refers to any substance that, when administered in a therapeutically effective amount to a patient suffering from a disease, has a therapeutic beneficial effect on the health and well-being of the patient. A therapeutic beneficial effect on the health and well-being of a patient includes, but is not limited to: (1) curing the disease; (2) slowing the progress of the disease; (3) causing the disease to retrogress; or (4) alleviating one or more symptoms of the disease.

As used herein, a bioactive agent also includes any substance that has a prophylactic beneficial effect on the health and well-being of the patient, when administered to a patient known or suspected of being particularly susceptible to a disease. A prophylactic beneficial effect includes, but is not limited to: (1) preventing or delaying on-set of a disease; (2) maintaining a disease at a retrogressed level once such level has been achieved by a therapeutically effective amount of a therapeutic agent, which may be the same as or different from the therapeutic agent used in a prophylactically effective amount; or (3) preventing or delaying recurrence of a disease after a course of treatment with a therapeutically effective amount of a therapeutic agent, which may be the same as or different from the therapeutic agent used in a prophylactically effective amount.

The amount of bioactive agent in a micelle of the invention will depend on the required minimum effective concentration (MEC) of the agent and the length of time over which it is desired that the MEC be maintained. For most bioactive agents the MEC will be known, or readily derivable by those skilled in the art from the literature. For experimental bioactive agents or those for which the MEC by localized delivery is not known, such can be empirically determined using techniques well-known to those skilled in the art.

Bioactive agents useful with the present invention include, without limitation, an anti-stenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cytoprotective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of antiproliferative agents include, without limitation, actinomycins, taxol, docetaxel, paclitaxel, rapamycin, 40-O-(3-hydroxyl)propyl-rapamycin, 40-O-[2-(2-hydroxyl)ethoxy]ethyl-rapamycin, or 40-O-tetrazole-rapamycin, 40-epi-(N1-tetrazolyl)-rapamycin, everolimus, biolimus, perfenidone and derivatives, analogs, prodrugs, co-drugs and combinations of any of the foregoing.

Examples of anti-inflammatory agents include, without limitation, both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, co-drugs and combinations of any of the foregoing.

Examples of antineoplastics and antimitotics include, without limitation, paclitaxel, docetaxel, methotrexate, azathioprine, vincristine, vinblastine, fluorouracil, doxorubicin hydrochloride, and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax a, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs, codrugs and combinations thereof.

Examples of cytostatic agents include, without limitation, angiopeptin, angiotensin converting enzyme inhibitors such as captopril, cilazapril or lisinopril, calcium channel blockers such as nifedipine; colchicine, fibroblast growth factor (FGF) antagonists, fish oil (ω-3-fatty acid), histamine antagonists, lovastatin, monoclonal antibodies such as, without limitation, those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of antiallergic agents include, without limitation, permirolast potassium.

Other compounds that may be used as bioactive agents of this invention include, without limitation, alpha-interferon, genetically engineered epithelial cells, dexamethasone, antisense molecules which bind to complementary DNA to inhibit transcription, and ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy, antiviral agents, analgesics and analgesic combinations, anorexics, antihelmintics, antiarthritics, antiasthmatic agents, anticonvulsants, antidepressants, antidiuretic agents, antidiarrheals, antihistamines, antimigrain preparations, antinauseants, antiparkinsonism drugs, antipruritics, antipsychotics, antipyretics, antispasmodics, anticholinergics, sympathomimetics, xanthine derivatives, cardiovascular preparations including calcium channel blockers and beta-blockers such as pindolol and antiarrhythmics, antihypertensives, diuretics, vasodilators including general coronary; peripheral and cerebral, central nervous system stimulants, cough and cold preparations, including decongestants, hypnotics, immunosuppressives, muscle relaxants, parasympatholytics, psychostimulants, sedatives, tranquilizers, naturally derived or genetically engineered lipoproteins, and derivatives, analogs, prodrugs, codrugs and combinations of any of the foregoing.

Micelles of the invention include one or more targeting ligands or one or more chelating agents bound to or integrated into the surface of the micelle.

A "targeting ligand" refers to a biochemical molecule that has, or a portion of which has, a particular affinity for another molecule that is expressed on the surface of a cell of a type that is found, preferably exclusively, at a diseased locale. When a micelle having a targeting ligand on its surface approaches a cell expressing the target molecule, the ligand binds to the molecule holding the micelle in place until it biodegrades and releases its payload of bioactive agent.

As used herein, "bound to" means the ligand is covalently or non-covalently coupled to the outer surface of the micelle. Covalent coupling refers to the formation of formal chemical bonds, wherein the bonded atoms share electron equally between them, between the ligand and the surface while non-covalent coupling can refer to ionic bonds, hydrogen bonding, van der Waals forces and the like wherein electrons are not shared equally between the atoms or groups effecting the coupling.

As used herein, "integrated into the surface of" means part of the ligand itself is part of the chemical structure of the material forming the micelle.

A non-limiting example of non-covalent coupling is the implementation of a hydrophobic lipid anchor. That is, a ligand with affinity for endothelium can be covalently bonded to the hydrophilic end of an amphiphilic molecule, such as a phospholipid. The other end of the amphiphile is a lipid—fatty acid—group that is capable of infiltrating the surface of the micelle and co-mingle with the hydrophobic entities that make up the core of the micelle. This embedded hydrophobic moiety is the "lipid anchor." These "lipid anchors" may be localized to the surface of a micelle by, without limitation, co-incubation of the groups with pre-made micelles, or by including these ligands during the micelle formulation process. The hydrophobic end of the amphiphile need not, however, necessarily be a lipid and the term "hydrophogic lipid anchor," as used herein, refers to any hydrophobic group that is capable of penetrating into the surface of a micelle and thereby anchor the entire molecule to the surface. Other means of localizing anchored ligands to the surface will become clear to those skilled in the art based on the disclosures herein and are within the scope of this invention.

The targeting ligand of the invention can include, without limitation, a polypeptide, a protein, an oligonucleotide, a lipid, a carbohydrate, a folate residue or a short chain alkyl group.

When the targeting ligand is a polypeptide, it can be selected from a group that includes a CRPPR (cysteine-arginine-proline-proline-arginine) polypeptide a peptidomimetic thereof or a homolog thereof, an ApoA1 mimetic peptide, an RGD (arginine-glycine-aspartic acid) sequence and an antibody fragment.

As used herein, "peptidomimetic" refers to a small protein-like chain designed to function like a peptide. They typically arise from modification of existing peptides in order to alter the peptide's properties such as, without limitation, the molecule's stability or biological activity.

As used herein, "homolog" refers both to chemical and biological derivative. Chemical homologs refer to compounds related by the inclusion of repetition of a single unit, usually a methylene (—$CH_2$—) group. Thus, pentane, $CH_3CH_2CH_2CH_2CH_3$, is a homolog of propane, ($CH_3CH_2CH_3$) and aminohexanoic acid, $NH_2(CH_2)_5COOH$, is a homolog glycine, $NH_2CH_2COOH$. A biological homolog refers to a structurally related peptide group derived from a common peptide.

It is to be understood that in some embodiments, a CRPPR polypeptide group can include more than one CRPPR group. That is a plurality of CRPPR groups may be linked together by, for example without limitation, aminohexanoic acid.

The CRPPR polypeptide has binding affinity for heart vein cells, heart capillary cells, heart artery cells or heart endothelial cells. Specifically, CRPPR binds to the heart-expressed proteins CRIP2, Sigirr, MpcII-3 and bc10. The present invention takes advantage of these binding properties to selectively deliver bioactive agent-containing micelles to the heart vasculature.

The CRPPR polypeptide, peptidomimetic or homolog thereof, can be anchored to a micelle by a lipophilic moiety that can include an oleyl group and additionally a poly(ethylene glycol) (PEG) group that connects the lipophilic moiety to the peptide group.

When the targeting ligand is a protein, it can be an antibody or antibody fragment selected from a group that includes an anti-intercellular adhesion molecule, an anti-vascular cellular adhesion molecule, an anti-integrin, an anti-platelet endothelial cell adhesion molecule, an anti-thrombomodulin, an anti-E-selectin, an anti-P-selectin, and anti-L-selectin, an anti-fibronectin, an anti-sialyl-Lewis glycan, an anti-endothelial clycocalyx protein, an anti-cadherin, an anti-vitronectin and any combination thereof.

When the ligand is a protein, it can also be an affibody.

As used herein, "affibody" refers to a relatively small synthetic protein molecule that has high binding affinity for a target protein. Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since it's binding site is approximately equivalent in surface area to the binding site of an antibody.

When the targeting ligand is an oligonucleotide, it can be an aptamer selected from a group that includes an anti-junction adhesion molecule and an anti-leukocyte adhesion molecule.

As used herein, an "aptamer" refers to an oligonucleic acid that has binding affinity for a specific target, e.g., without limitation, a protein, a nucleic acid, a specific whole cell or a particular tissue. Aptamers can be obtained by in vitro selection from a large random sequence pool of nucleic acids, although natural aptamers are also encompassed by the present invention.

When the targeting ligand is a lipid, it can be selected from a group that includes fatty acids such as, without limitation, oleic acid or stearic acid, derivative of fatty acids such as, without limitation, monoglycerides, diglycerides, triglycerides, phospholipids and ceramide. As used herein, "fatty acid" refers to an unbranched aliphatic hydrocarbon chain terminated by a carboxyl group.

Preferably at present, a fatty acid of this invention comprises from four (butyric acid) up to about 28 carbon atoms. The fatty acid may be saturate or unsaturated.

Micelles of the invention may have one or more chelating agents covalently bound to or integrated into the surface of the micelles as the targeting moiety. For example, it is possible for a chelating agent(s) to be covalently bound to the surface of the micelle through a PEG chain, with or without a cleavable linker. Alternatively, it is possible for the chelating agent(s) to directly attach to the surface of the micelle by a portion of the agent itself.

As used herein, "chelating agent" refers to a chemical compound that can form a multivalent complex with a metal substrate. For example, the chelating agent EDTA will bind to calcium through at least two coordination sites, thereby forming a multivalent calcium-EDTA complex.

The one or more chelating agents of the invention can be selected from a group that includes, but is not limited to, ethylenediamine tetraacetic acid (EDTA), diethylenetriamine pentaacetic acid (DTPA), N-(2-hydroxyethyl)ethylenedinitrilotriacetic acid (HEDTA), nitrilotriacetic acid (NTA), citrate, tetracycline, ethylene diamine disuccinic acid, ethylene diaminebis, O-hydroxyphenyl acetic acid and ethylene diamine-N,N' diacetic acid, and derivatives thereof.

Because atherosclerotic lesions and infarcted myocardial tissues are known to possess high levels of calcium in their tissues, the chelating agents of the invention will preferentially act as targeting ligands. Infarcted myocardial tissue refers to heart tissue to which the supply of blood has been interrupted, while myocardial infarction refers to the medical condition that occurs when the supply of blood to a part of the heart has been interrupted. An important risk factor of myocardial infarction is atherosclerosis.

Micelles of the invention will also include a PEG group operatively coupled to the surface of the micelle.

As used herein, "operatively coupled" refers to the attachment of a PEG group to the surface of a micelle through either direct or indirect means. For example, it is possible for the PEG group to directly attach to the micelle surface by a portion of the PEG group itself. Alternatively, it is possible for the PEG group to be attached to the surface of the micelle through a cleavable linker as described elsewhere herein.

Micelles with PEG on their surface have an increased ability to evade detection by a host's immune system over micelles without PEG on their surface. This increased ability allows PEG-modified micelles more time to move through the vasculature, thereby allowing the targeting ligands more time to selectively target diseased tissues of the vasculature.

In a presently preferred aspect of the invention, the PEG group is operatively coupled to the surface of the micelle through a cleavable linker. As used herein, a "cleavable linker" refers to a molecule that at or near one end has a functional group selected so as to be able to chemically bond to a targeting moiety or a protective moiety such as poly(ethylene glycol). At the other end is a functional group that is selected so as to chemically bond to the surface of the micelle. It is, of course, possible to pre-select both the materials that make up the micelle and the materials making up the cleavable linker such that selected functional groups that will react with one another are present on the two entities. In addition to the end groups a cleavable linker has, somewhere in its structure, a functionality that is susceptible to cleavage under physiological conditions or, if preferred, are induced to cleave under the influence of an external stimulus.

Thus, a cleavable linker may include a photoreactive group, an ester, an azo linkage, a hydrazone, an orthoester, a boron complex, an imino carbonate, a Schiff base, a hemi-acetal, an acetal, a ketal, a hemi-ketal, an enzymatically cleavable peptide, an analyte-receptor complex, a group susceptible to oxidative cleavage, a group susceptible to reductive cleavage or a cyclodextrin complex which can include a cyclodextrin-adamantane complex. Methods of attaching a cleavable linker to PEG and a nanoparticle are known to those skilled in the art and can be employed in the present invention. See U.S. Pat. No. 7,108,863 to Zalipsky et al. In various aspects, the cleavable linker further comprises a hydrophobic lipid anchor. In this aspect, the hydrophobic lipid anchor can include a degradable polymer selected from a group that includes poly(lactic acid), poly(glycolic acid), poly(L-lactic acid), poly(DL-lactic acid), poly(lactic-co-glycolic acid), poly(butyl acrylate), polycaprolactone and parylene. In this aspect, the hydrophobic lipid anchor can include a lysolipid or a di-acyl phospholipid.

In various aspects, the analyte-receptor complex comprises streptavidin-biotin.

In various aspects, the cleavable linker comprises a cyclodextrin complex which can include a cyclodextrin-adamantane complex.

An aspect of the present invention relates to a method for targeting an atherosclerotic lesion or infarcted myocardial tissue that involves providing a chelating agent composition according to the invention and administering the composition to a patient known or suspected of having such an ailment. The chelating agent present on the surface of the micelle will act to target calcium in the afflicted tissues An aspect of the invention relates to an implantable medical device that includes a device body and a composition according to the invention disposed over the device body.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, PFO closure devices, arterial closure devices, artificial heart valves and cerebrospinal fluid shunts.

An implantable medical device specifically designed and intended solely for the localized delivery of a therapeutic agent is within the scope of this invention.

At present, a preferred implantable medical device comprises a stent.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. Indeed, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. Due to the expansion of the stent, a stent coating must be flexible and capable of elongation.

Exemplary stent materials include, but are not limited to, stainless steel, nitinol, tantalum, tantalum alloy, titanium, titanium alloy, cobalt chromium, alloy x, niobium, niobium alloy, zirconium and zirconium alloy.

As used herein, "device body" refers to a fully formed implantable medical device with an outer surface to which no coating or layer of material different from that of which the device itself is manufactured has been applied. "Outer surface" means any surface, however spatially oriented, that is in contact with bodily tissue or fluids. An example of a "device body" is a BMS, i.e., a bare metal stent, which is a fully-formed usable stent that has not been coated with a layer of any material different from the metal of which it is made. It is to be understood that device body refers not only to BMSs but also to any uncoated device regardless of what it is made.

As use herein, a material that is described as being "disposed over" an indicated substrate, e.g., without limitation, a device body, refers to a relatively thin coating of a material applied to all or a portion of the exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate. the intervening layer may be, for example without limitation, a primer layer that facilitates the adhesion of the material being "disposed over" to the substrate.

An aspect of the invention relates to a method for treating or preventing a disease that involves implanting a medical device according to the invention in a patient in need thereof. Methods of implanting a medical device are known to those skilled in the art.

A "patient" refers to any species that might benefit from treatment using the method herein but at present is preferably a mammal and most preferably a human being.

As used herein, "treating" refers to the administration of a therapeutically effective amount of a bioactive agent to a patient known or suspected to be suffering from a vascular disease.

A "therapeutically effective amount" refers to that amount of a therapeutic agent that will have a beneficial effect, which may be curative or palliative, on the health and well-being of the patient so afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period of about an hour to about 3 days. Medium-term sustained release refers to administration of a therapeutically effective amount of a therapeutic agent over a period of about 3 days to about 4 weeks and long-term refers to the delivery of a therapeutically effective amount over any period in excess of about 4 weeks, but in particular at present about 4 weeks to about a year.

As used herein, "known" to be afflicted with a disease refers first to a condition that is relatively readily observable and/or diagnosable. An example, without limitation, of such a disease is atherosclerosis, which is a discrete narrowing of a patient's arteries.

As used herein, "vascular disease locale" refers to the location within a patient's body where an atherosclerotic lesion(s) is present, where stenosis may develop or the site of vulnerable plaque(s).

An atherosclerotic lesion refers to a deposit of fatty substances, cholesterol, cellular waste products, calcium and/or fibrin on the inner lining or intima of an artery.

Stenosis refers to the narrowing or blockage of an artery.

Vulnerable plaque is quite different from either atherosclerosis or stenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

Another aspect of the invention relates to a method for treating or preventing a disease that involves providing a composition according to the invention and administering a therapeutically effective amount of the composition to a patient in need thereof.

In various aspects, administering the composition comprises intra-arterial delivery including percutaneous transluminal coronary arterial delivery and using a catheter.

Diseases that may be treated by this method include, but are not limited to, atherosclerosis, stenosis and vulnerable plaque.

It is to be understood that once micelles are selectively targeted, PEG can be released from the micelle via scission of the cleavable linker. The micelle can then be recognized by the host's immune system. When this happens, the bioactive agent-loaded micelles can be internalized by inflammatory phagocytes where they will release bioactive agent, thereby killing the phagocytes. In addition, once bioactive agent-containing micelles are selectively targeted to atherosclerotic lesions and/or infarcted myocardial tissues, exposure to physiological conditions can cause the micelles to degrade and release bioactive agent. Physiological conditions refers to the physical, chemical and biochemical milieu that constitutes the mammalian body and includes, without limitation, pH, temperature, enzymes and the presence of destructive cells such as phagocytes.

Methods of providing sustained release of bioactive agent from micelles are also encompassed by the present invention. For example, sustained release of agent from a micelle can be accomplished by increasing the initial agent loading to such an extent that the agent crystallizes in the micelle core, thereby forming a more stable phase than if the agent did not crystallize.

Sustained release can also be accomplished by incorporating a crystalline solid, e.g., calcium phosphate, into the core of the micelle. The agent can localize within the crystalline solid, thereby preventing the immediate release of agent upon tissue uptake of the micelle.

Alternatively, the micelle hydrophobic core can be partially or fully cross-linked. For example, the hydrophobic section of a di- or tri-block copolymer can be chosen to include one or more vinyl groups. After preparing the micelle with an entrapped bioactive agent, an initiator can be added to crosslink the vinyl groups. The extent of cross-linking can be controlled by varying the amount of initiator and/or the amount of time in which the initiator is allowed to act.

Another method for providing sustained release micelles involves the use of temperature-dependent micelles. Specifically, the glass transition temperature of the micelle core materials can be varied for controlled agent release by selecting different ratios of polymer blocks in the di- and tri-block copolymers. Upon judicious selection of the blocks, a polymer with a glass transition temperature slightly above body temperature, i.e., above 37° C. will be produced, methods of which are known to those skilled in the art. Because diseased tissues, e.g., atherosclerotic lesions, are known to have slightly higher temperatures than normal body temperature, the micelle, when it is at its glass transition temperature, will become soft and unstable, thus facilitating the release of active agent at the site of diseased tissue.

A further method for providing sustained release micelles involves the use of di- or tri-block copolymers in which a single block can be chosen to be biodegradable, thereby providing a sustained release micelle.

Even in diseased tissue however, the variation of body temperature rarely exceeds a few degrees, thus, temperature-dependent micelles may require a external stimulus to become soft and unstable. For example, a catheter-based system which controllably and safely increases the local temperature at a delivery site or an external heat source to increase the local temperature few degrees, e.g., a far infrared laser or a micro wave device, can be used. Methods of using such devices are known to those skilled in the art. Examples of micelle materials that can be used for temperature-dependent aspects of the invention include the shell materials PEG or a di- or tri-block copolymer consisting of PEG and another hydrophilic polymer. The micelle core can be composed of, but is not limited to, PLGA, PLA, PGA, pH sensitive polymers: poly(N-isoproprlacrylamide) (pNIPPAM) and its derivatives such as pNIPPAM-PLA, pNIPPAM-PLGA, pNIPPAM-PCL or di- or tri-block copolymers of the aforementioned.

In another embodiment, the micelle can have a magnetic core so that a fluctuating magnetic field would raise the local temperature inside the core to cause micelle destabilization and release of active agent.

In further aspects of the invention, the hydrophobic component of the micelle could be substituted with a fatty acid or the ratio of degradable to stable components in the micelle can be changed, both methods of which would provide for sustained release micelles.

Micelles of the invention can possess other triggered release capabilities as well. For example, ultrasound-, light- or other-sensitive bioactive agent-loaded micelles can be used. Once the micelles are located at an atherosclerotic lesion or at infarcted myocardial tissues, the micelles can be triggered to release the bioactive agent by light activation or ultrasound. This may be done locally through a catheter-based intervention, e.g., light, or globally, e.g., by ultrasound triggering.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition for targeted delivery of a bioactive agent to diseased tissues of the vasculature, comprising:
 a micelle;
 a bioactive agent encapsulated within, adhered to a surface of or integrated into the structure of the micelle;
 a targeting ligand,
  wherein the targeting ligand is a chelating agent that targets the micelle to calcium in the diseased tissue of the vasculature,
   wherein the chelating agent is covalently bound to or integrated into the surface of the micelle, and
   wherein the chelating agent is selected from the group consisting of ethylenediamine tetraacetic acid, diethylenetriamine pentaacetic acid, N-(2-hydroxyethyl)ethylenedinitrilotriacetic acid, nitrilotriacetic acid, citrate, tetracycline, ethylene diamine disuccinic acid, ethylene diaminebis, O-hydroxyphenyl acetic acid, ethylene diamine-N,N' diacetic acid, derivatives thereof and combinations thereof; and
 a poly(ethylene glycol) group operatively coupled to the surface of the micelle through a cleavable linker.

2. The composition according to claim 1, wherein the cleavable linker is selected from the group consisting of a photoreactive moiety, an ester, an azo linkage, a hydrazone, an orthoester, a boron complex, an imino carbonate, a Schiff base, a hemi-acetal, an acetal, a ketal, a hemi-ketal, an enzymatically cleavable peptide, an analyte-receptor complex, a group susceptible to oxidative cleavage, or a group susceptible to reductive cleavage.

3. The composition according to claim 2, wherein the cleavable linker further comprises a hydrophobic lipid anchor.

4. The composition according to claim 3, wherein the hydrophobic lipid anchor comprises a lysolipid or a di-acyl phospholipid.

5. The composition according to claim 3, wherein the hydrophobic lipid anchor comprises a biocompatible, biodegradable polymer.

6. The composition according to claim 5, wherein the biocompatible, biodegradable polymer is selected from the group consisting of poly(lactic acid), poly(glycolic acid), poly(L-lactic acid), poly(DL-lactic acid), poly(lactic-co-glycolic acid), poly(butyl acrylate), polycaprolactone and parylene.

7. The composition according to claim 2, wherein the analyte-receptor complex comprises streptavidin-biotin.

8. The composition according to claim 1, wherein the cleavable linker comprises a cyclodextrin complex.

9. The composition according to claim 1, wherein the bioactive agent is selected from the group consisting of an anti-stenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardio-protective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor and combinations thereof.

10. A method for treating a disease comprising administering a therapeutically effective amount of the composition of claim 1 to a patient in need thereof.

11. The method according to claim 10, wherein the disease comprises a vascular disease selected from the group consisting of atherosclerosis, stenosis, restenosis and vulnerable plaque.

12. The method according to claim 10, wherein administering the composition comprises intra-arterial delivery.

13. The method according to claim 12, wherein intra-arterial delivery comprises percutaneous transluminal coronary arterial delivery.

14. The method according to claim 12, wherein intra-arterial delivery comprises using a catheter.

* * * * *